(12) United States Patent
Wagner et al.

(10) Patent No.: US 12,138,399 B2
(45) Date of Patent: Nov. 12, 2024

(54) SENSOR ASSEMBLY WITH IMPROVED PERFORMANCE AND CONNECTION

(71) Applicant: Measurement Specialties, Inc., Hampton, VA (US)

(72) Inventors: Chris Wagner, Fremont, CA (US); Kejin Wang, Fremont, CA (US)

(73) Assignee: TE CONNECTIVITY SOLUTIONS GMBH, Schaffhausen (CH)

( * ) Notice: Subject to any disclaimer, the term of this patent is extended or adjusted under 35 U.S.C. 154(b) by 280 days.

(21) Appl. No.: 17/513,024

(22) Filed: Oct. 28, 2021

(65) Prior Publication Data

US 2023/0134544 A1    May 4, 2023

(51) Int. Cl.
  *A61M 25/00*    (2006.01)
  *A61B 5/00*    (2006.01)
  *G01L 9/00*    (2006.01)

(52) U.S. Cl.
  CPC ........... *A61M 25/00* (2013.01); *A61B 5/6852* (2013.01); *A61B 2562/0247* (2013.01); *A61M 2025/0002* (2013.01); *G01L 9/0052* (2013.01)

(58) Field of Classification Search
  None
  See application file for complete search history.

(56) References Cited

U.S. PATENT DOCUMENTS

| | | | |
|---|---|---|---|
| 7,731,664 B1 * | 6/2010 | Millar | A61B 5/0215 600/488 |
| 9,289,137 B2 * | 3/2016 | Corl | A61B 5/0215 |
| 10,470,713 B2 * | 11/2019 | Mahlin | A61B 5/6851 |
| 2014/0180141 A1 * | 6/2014 | Millett | A61B 5/0215 29/857 |
| 2014/0257105 A1 * | 9/2014 | Dausch | A61B 8/4281 600/458 |
| 2018/0310839 A1 * | 11/2018 | McCaffrey | A61B 5/02158 |

FOREIGN PATENT DOCUMENTS

| | | |
|---|---|---|
| CN | 105744951 A | 7/2016 |
| CN | 111787841 A | 10/2020 |
| CN | 112674734 A | 4/2021 |
| JP | 2010230694 A | 10/2010 |

OTHER PUBLICATIONS

Japanese Office Action with English translation thereof, dated Oct. 10, 2023 in Application No. 2022170357, 6 pages.
Partial European Search Report European Application No. 22203544. 6-1113, European Filing Date, Mar. 2023.
Chinese Office Action with English translation thereof, dated May 10, 2024 in Application No. 20221130973.2, 21 pages.

* cited by examiner

*Primary Examiner* — John E Breene
*Assistant Examiner* — Nigel H Plumb

(57) ABSTRACT

A sensor assembly includes a carrier having a base wall and a pair of side walls extending from the base wall, and a sensor mounted on the base wall between the side walls. Each of the side walls has a side step between a first side section and a second side section extending from the first side section along a longitudinal direction of the carrier. A sensor die of the sensor is spaced in a width direction perpendicular to the longitudinal direction by a first lateral gap distance from the first side section and by a second lateral gap distance from the second side section. The second lateral gap distance is greater than the first lateral gap distance.

20 Claims, 12 Drawing Sheets

SENSOR ASSEMBLY WITH IMPROVED PERFORMANCE AND CONNECTION

FIELD OF THE INVENTION

The present invention relates to a sensing device and, more particularly, to a sensor assembly of the sensing device.

BACKGROUND

Catheters for invasive human body procedures, as well as other applications, use pressure sensors to improve existing procedures or conduct new procedures. The sensors are frequently small and fragile, and are difficult to install in the catheter without damaging the sensor. During insertion of the sensor into the catheter, the sensor can contact the walls of the catheter, resulting in damage to the sensor and unreliable sensor performance. Mounting the sensor in the proper location in the catheter is also difficult. In some applications, conditioning electronics connected to the sensor must first be removed before the sensor is carefully placed in the catheter, then the wires must be re-attached. The complicated re-attachment of the wires impairs the reliability of the electrical connection and the signal from the sensor. The sensor is also difficult to adhesively attach to the catheter in the proper orientation due to curing and positioning limitations in small spaces.

SUMMARY

A sensor assembly includes a carrier having a base wall and a pair of side walls extending from the base wall, and a sensor mounted on the base wall between the side walls. Each of the side walls has a side step between a first side section and a second side section extending from the first side section along a longitudinal direction of the carrier. A sensor die of the sensor is spaced in a width direction perpendicular to the longitudinal direction by a first lateral gap distance from the first side section and by a second lateral gap distance from the second side section. The second lateral gap distance is greater than the first lateral gap distance.

BRIEF DESCRIPTION OF THE DRAWINGS

The invention will now be described by way of example with reference to the accompanying Figures, of which.

DETAILED DESCRIPTION OF THE EMBODIMENT(S)

Figure 1:
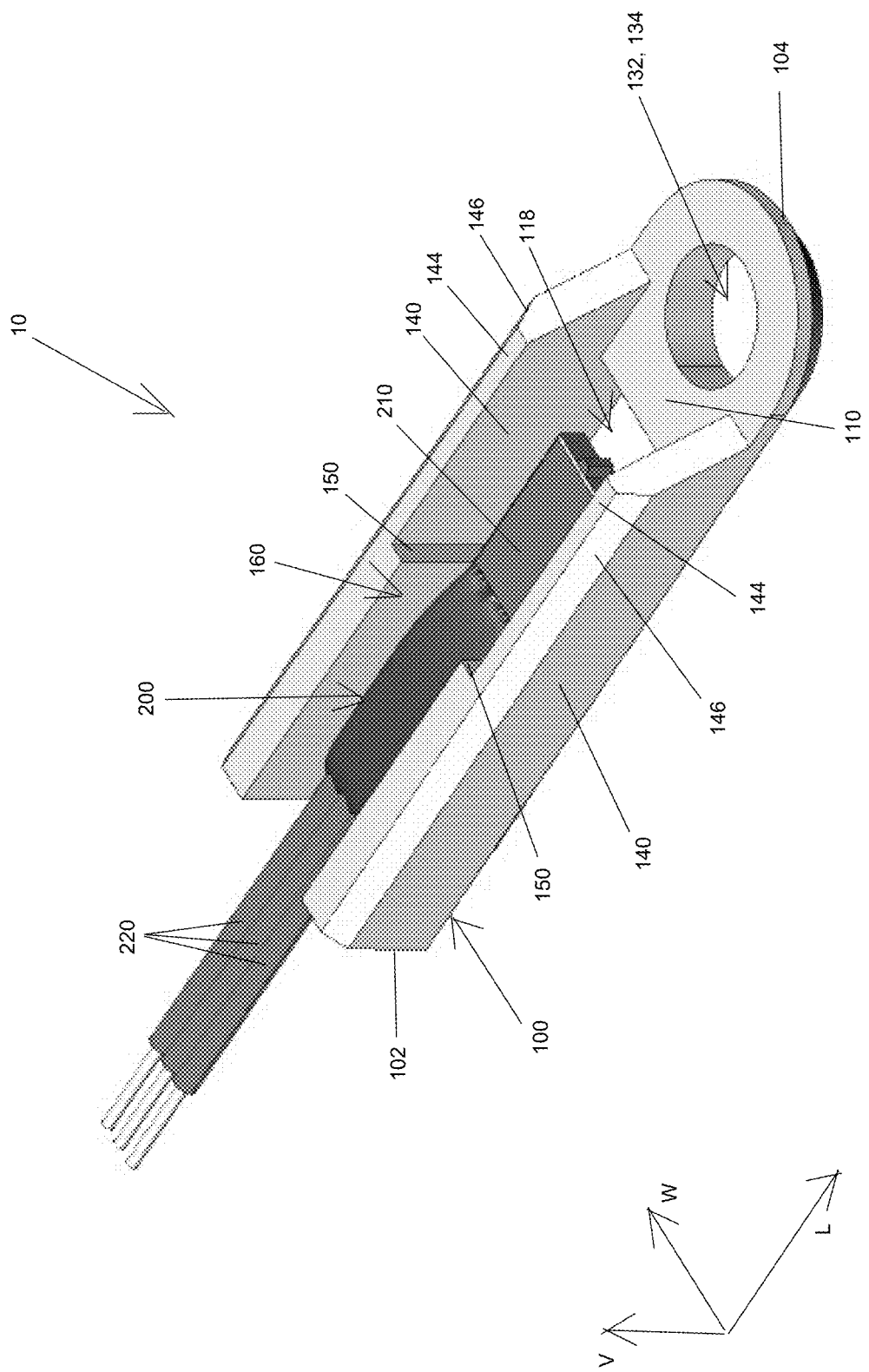
FIG. 1 is a perspective view of a sensor assembly according to an embodiment.

Exemplary embodiments of the present disclosure will be described hereinafter in detail with reference to the attached drawings, wherein like reference numerals refer to like elements. The present disclosure may, however, be embodied in many different forms and should not be construed as being limited to the embodiments set forth herein; rather, these embodiments are provided so that the present disclosure will convey the concept of the disclosure to those skilled in the art. In addition, in the following detailed description, for purposes of explanation, numerous specific details are set forth in order to provide a thorough understanding of the disclosed embodiments. However, it is apparent that one or more embodiments may also be implemented without these specific details.

Throughout the specification, directional descriptors are used such as "longitudinal", "width", and "vertical". These descriptors are merely for clarity of the description and for differentiation of the various directions. These directional descriptors do not imply or require any particular orientation of the disclosed elements.

Throughout the drawings, only one of a plurality of identical elements may be labeled in a figure for clarity of the drawings, but the detailed description of the element herein applies equally to each of the identically appearing elements in the figure.

Figure 6:
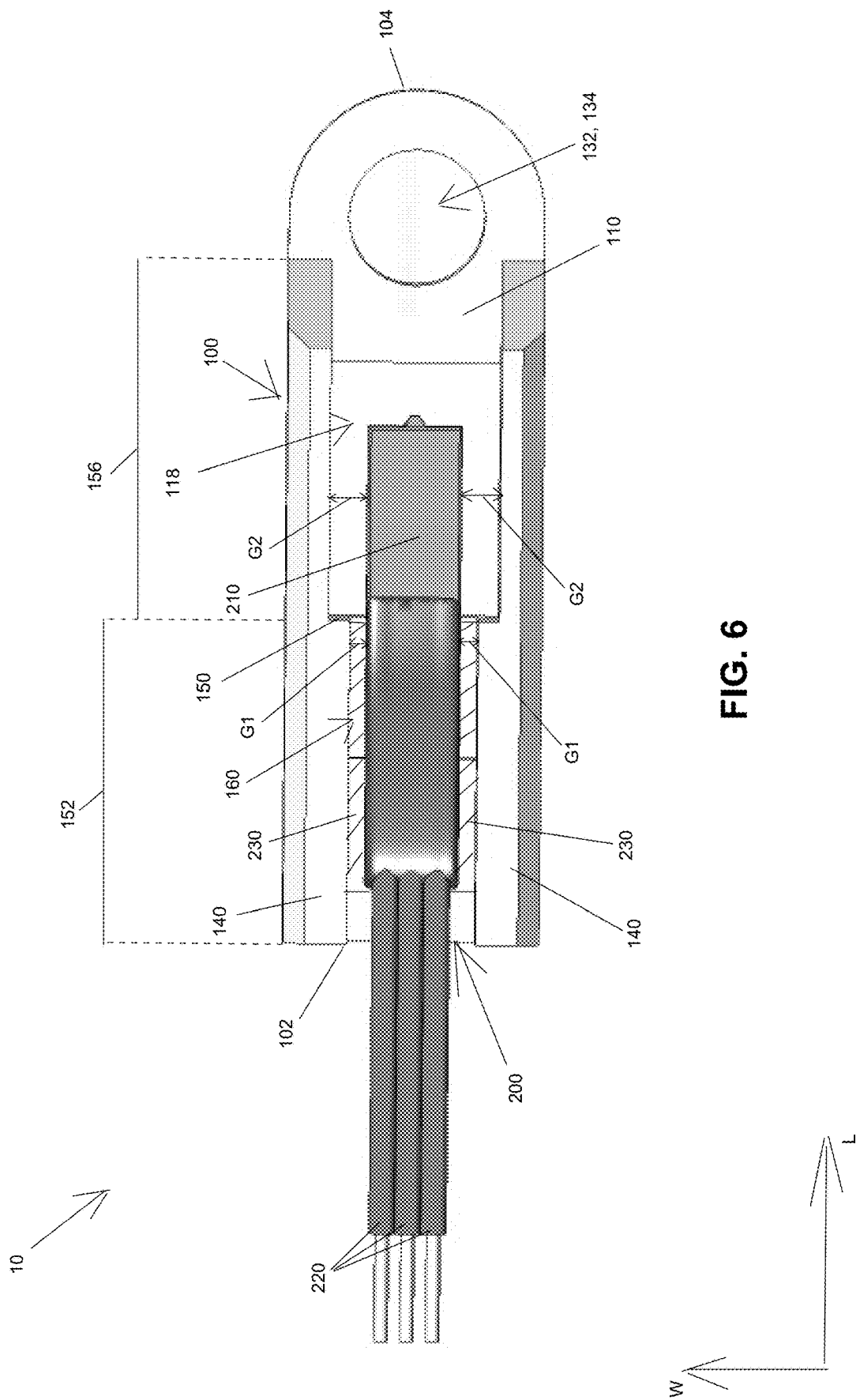
FIG. 6 is a top view of the sensor assembly.
Figure 7:
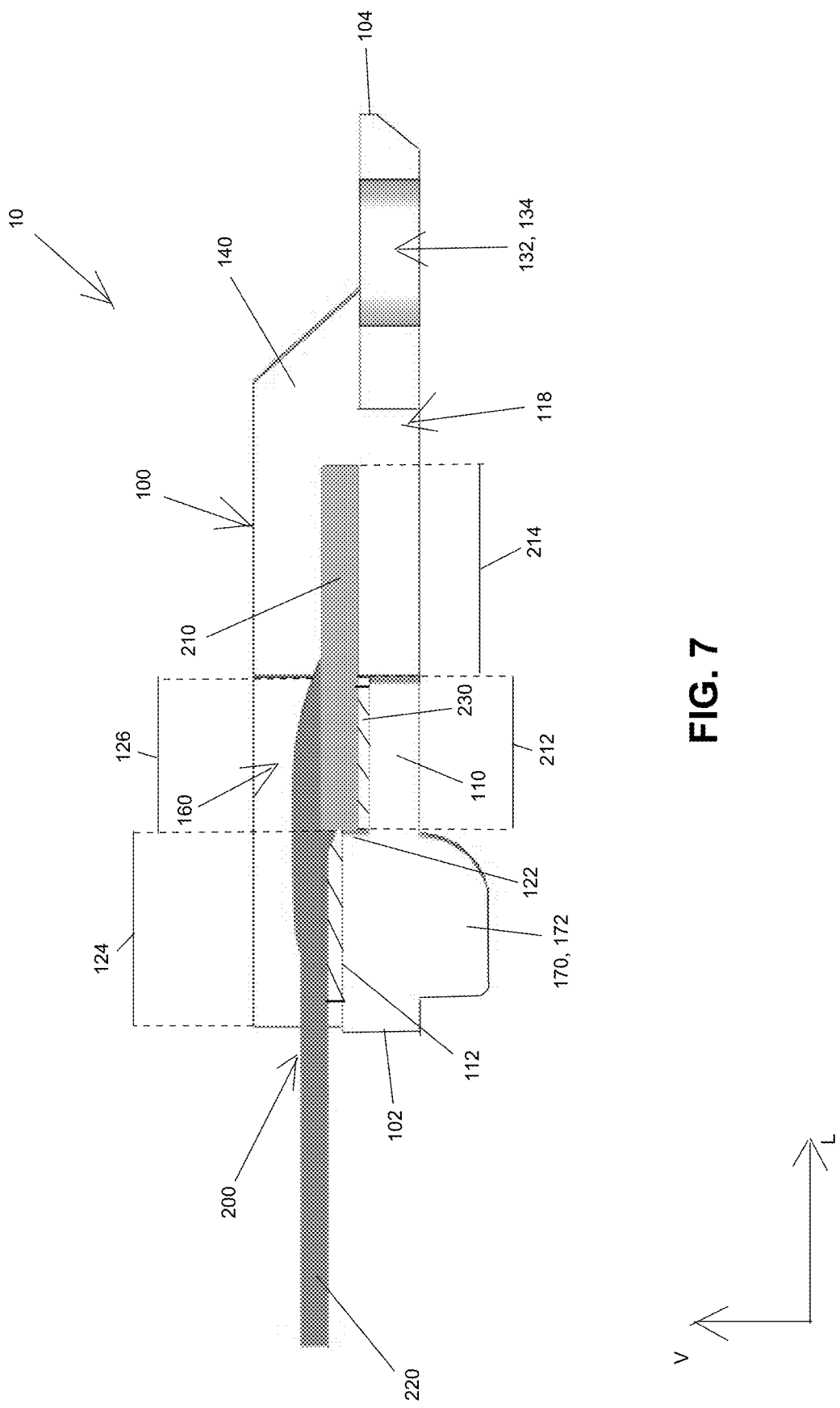
FIG. 7 is a sectional side view of the sensor assembly.

A sensor assembly 10 according to an embodiment is shown in FIGS. 1, 6, and 7. The sensor assembly 10 includes a carrier 100 and a sensor 200 mounted on the carrier 100.

Figure 2:
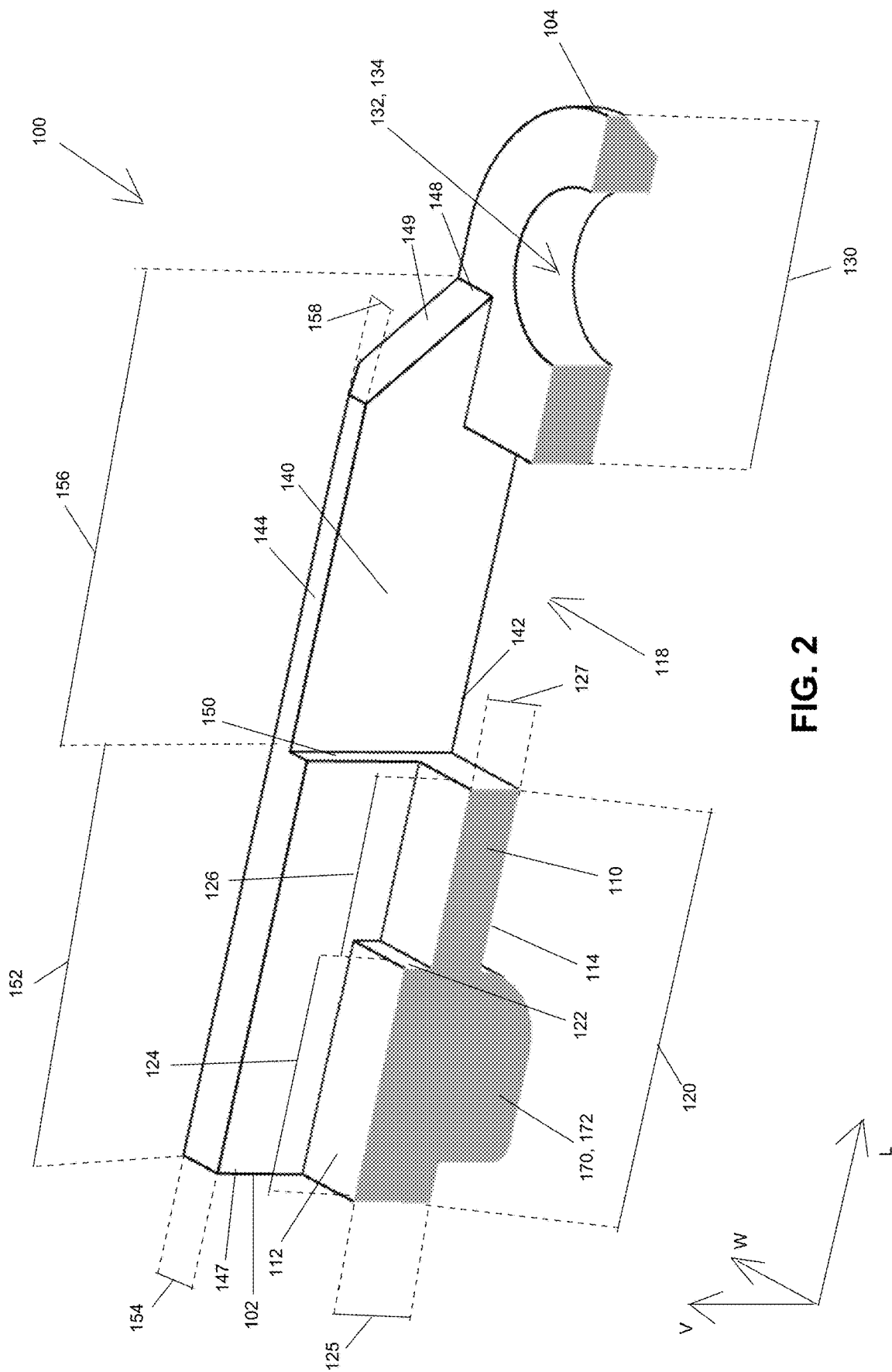
FIG. 2 is a sectional perspective view of a carrier of the sensor assembly.
Figure 3:
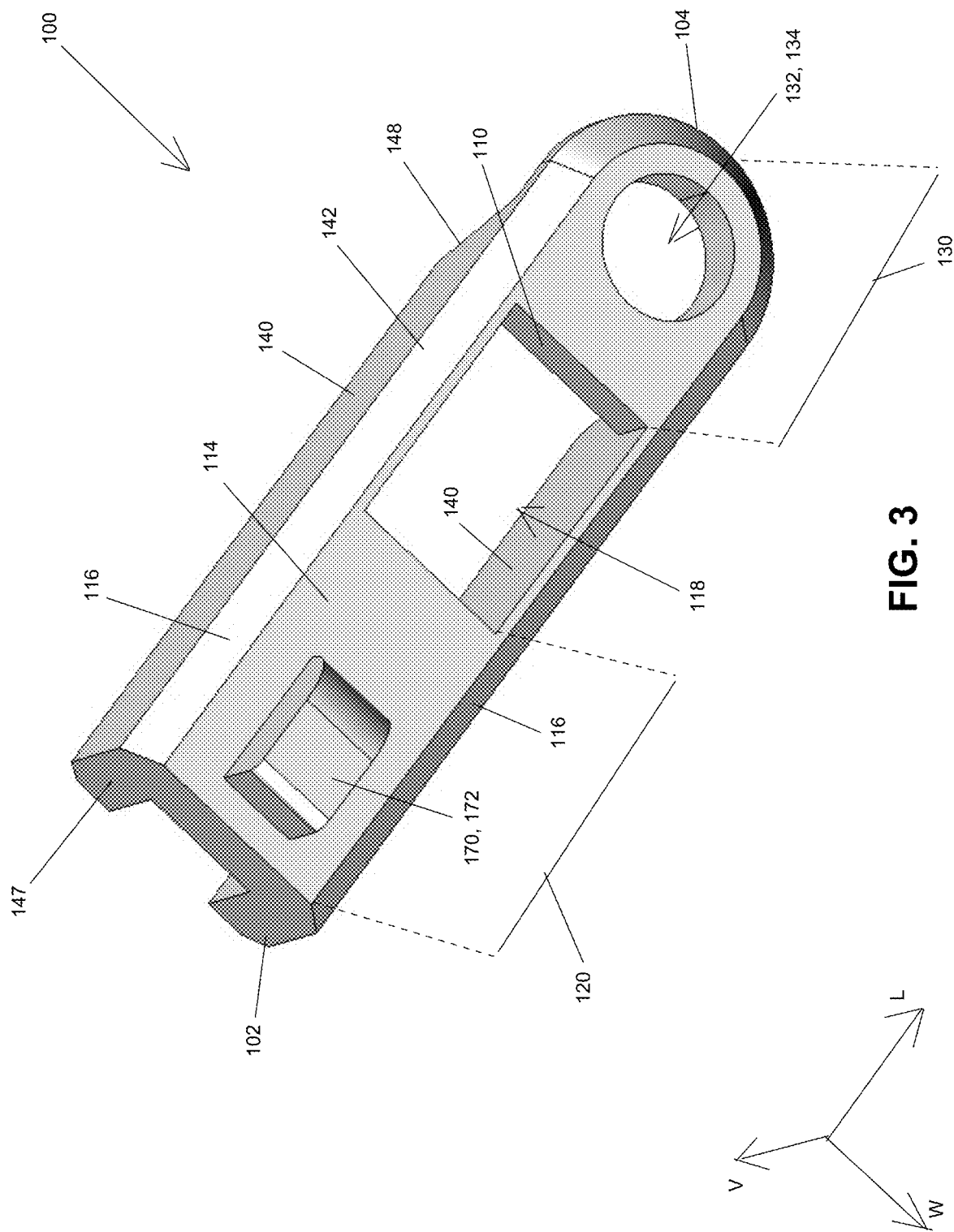
FIG. 3 is a bottom perspective view of the carrier.

The carrier 100, as shown in FIGS. 1-3, extends from a proximal end 102 to a distal end 104 along a longitudinal direction L of the carrier 100. The carrier 100 has a base wall 110 extending between the proximal end 102 and the distal end 104 and a pair of side walls 140 extending from the base wall 110 in a vertical direction V perpendicular to the longitudinal direction L. The base wall 110 and the side walls 140 define a sensor receiving space 160 shown in FIG. 1.

The base wall 110, as shown in FIGS. 2 and 3, has a sensing opening 118 extending through the base wall 110 in the vertical direction V. In another embodiment, the sensing opening 118 could be a recess in the base wall 110 facing the sensor receiving space 160 that does not extend fully through the base wall 110 in the vertical direction V. The base wall 110 has a rear base section 120 at the proximal end 102 and a front base section 130 at the distal end 104 separated from the rear base section 120 along the longitudinal direction L by the sensing opening 118.

As shown in FIG. 2, the rear base section 120 has a base step 122 between a first base step section 124 at the proximal end 102 and a second base step section 126 extending from the first base step section 124. The first base step section 124 has a first base thickness 125 along the vertical direction V and the second base step section 126 has a second base thickness 127 along the vertical direction V. The first base thickness 125 is greater than the second base thickness 127.

The front base section 130, as shown in FIGS. 2 and 3, has a pulling device 132. In the embodiment shown in FIGS. 2 and 3, the pulling device 132 is an eyelet 134 extending through the base wall 110 in the vertical direction V. In the shown embodiment, the eyelet 134 is a symmetrical, circular passageway extending through the base wall 110. In other embodiments, the eyelet 134 may be a passageway of any other shape extending through the base wall 110, including any symmetrical or asymmetrical shape.

Figure 4:
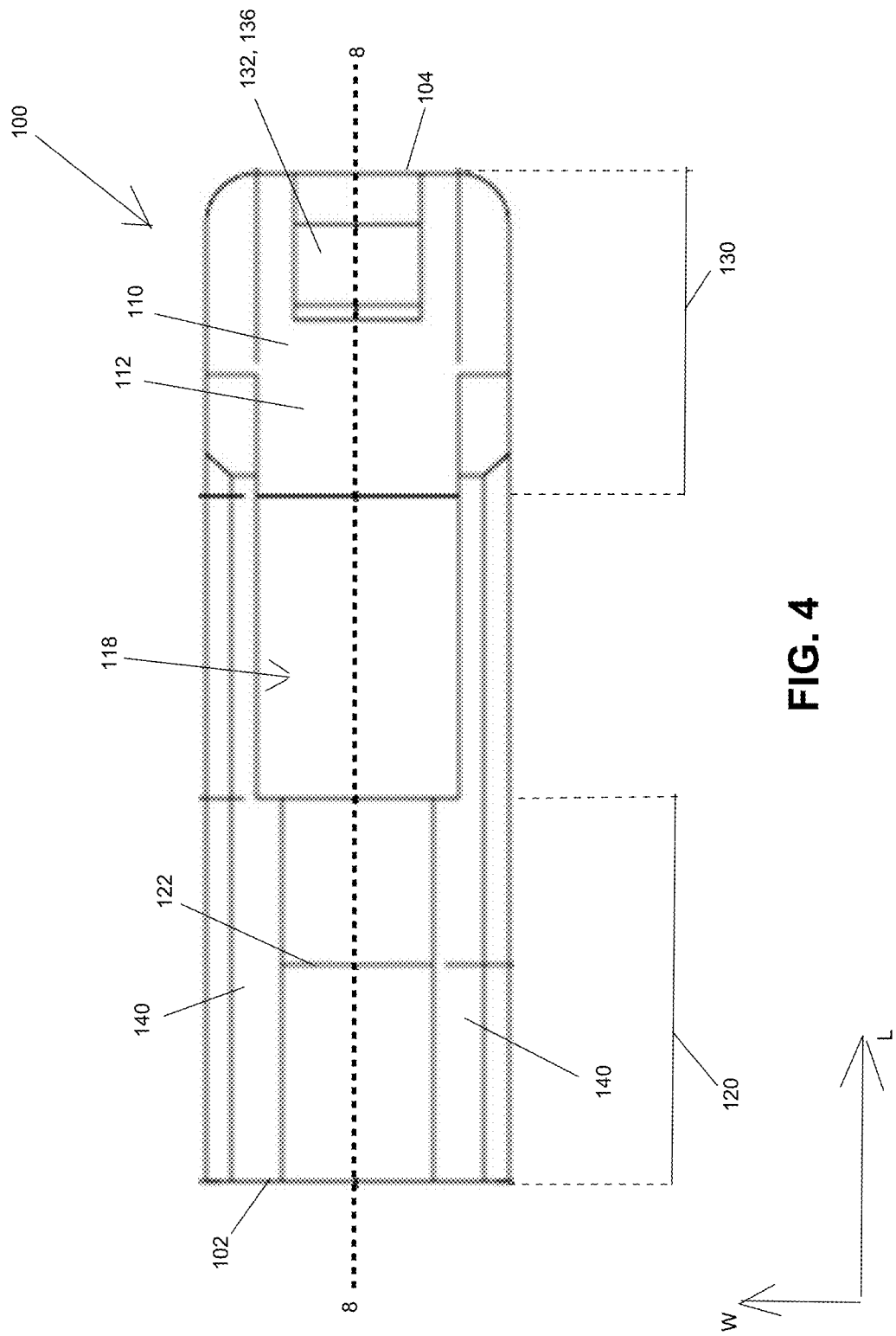
FIG. 4 is a top view of a carrier according to another embodiment.
Figure 5:
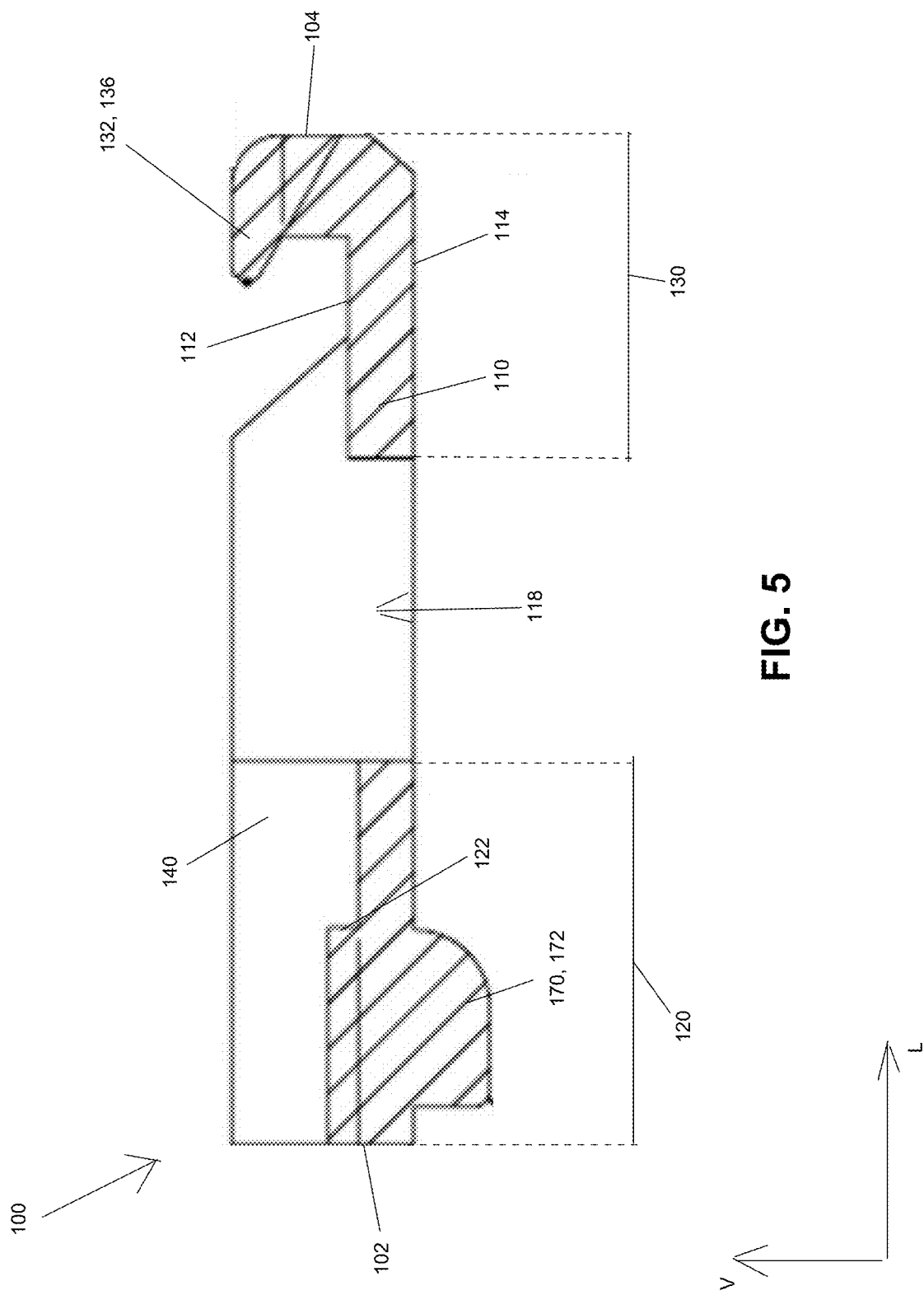
FIG. 5 is a sectional side view of the carrier of FIG. 4.

In another embodiment shown in FIGS. 4 and 5, the pulling device 132 in the front base section 130 is a hook 136 extending from an inner base surface 112 of the base wall 110 in the vertical direction V; as shown in FIGS. 2, 4, and 5, the base wall 110 has the inner base surface 112 and an outer base surface 114 opposite the inner base surface 112 in the vertical direction V. The hook 136 shown in FIGS. 4 and 5 is merely exemplary and, in other embodiments, the hook 136 may be any element that extends from the inner base surface 112 of the base wall 110 in the vertical direction V, may be positioned asymmetrically or symmetrically on the carrier 100, and may be a single hook 136 or a plurality of hooks 136 positioned in any arrangement. In other embodiments, the pulling device 132 in the front base section 130 may be any other type of recess or protrusion that is capable of being engaged and pulled by an external element, as described in greater detail below.

Each of the side walls 140, as shown in FIG. 2, has a base end 142 connected to a side of the base wall 110 and a free end 144 opposite the base end 142 in the vertical direction V. Each of the side walls 140 extends along the longitudinal direction L from a first end 147 to an opposite second end 148. In the shown embodiment, the second end 148 has a sloped shape 149 that is inclined with respect to the vertical direction V and the longitudinal direction L.

As shown in FIG. 1, each of the side walls 140 has a side step 150. The side step 150, as shown in FIG. 2, is between a first side section 152 and a second side section 156 of the side wall 140. The second side section 156 extends from the first side section 152 along the longitudinal direction L. The first side section 152 has a first side thickness 154 in a width direction W perpendicular to the vertical direction V and the longitudinal direction L. The second side section 156 has a second side thickness 158 in the width direction W. The first side thickness 154 is greater than the second side thickness 158.

At the free end 144, each of the side walls 140 has a profiled side edge 146, as shown in FIG. 1, on a side facing away from the sensor receiving space 160. In the shown embodiment, the profiled side edge 146 is a straight chamfer intersecting the free end 144. In other embodiments, the profiled side edge 146 could have a curved cross-sectional shape.

The base wall 110 has a profiled base edge 116, as shown in FIG. 3, on opposite sides of the outer base surface 114 of the base wall 110 in the width direction W. Each of the profiled base edges 116, in the shown embodiment, is a straight chamfer intersecting the base end 142 of one of the side walls 140. In other embodiments, the profiled base edges 116 could have a curved cross-sectional shape. The shape of the profiled base edges 116 corresponds to the shape of the profiled side edges 146 in an embodiment. In another embodiment, the shape of the profiled base edges 116 may be different from the shape of the profiled side edges 146, provided that the profiled base edges 116 and the profiled side edges 146 serve the function described below. In another embodiment, the profiled base edges 116 and the profiled side edges 146 could be omitted.

The carrier 100, as shown in FIGS. 2 and 3, has a carrier positioning device 170 in the rear base section 120. In the shown embodiment, the carrier positioning device 170 is a peg 172 disposed on the outer base surface 114 of the base wall 110 and extending from the outer base surface 114 in the vertical direction V. In other embodiments, the carrier positioning device 170 can be any other type of protrusion extending from the outer base surface 114. In the shown embodiment, the carrier positioning device 170 is a single peg 172 positioned approximately centrally on the outer base surface 114; in other embodiments, the carrier positioning device 170 could be one peg 172 positioned off-center or asymmetrically on the outer base surface 114, or could be a plurality of pegs 172 positioned symmetrically or asymmetrically on the outer base surface 114. In further embodiments, for example as described below, the carrier positioning device 170 can be a recess extending through the base wall 110 in the vertical direction V, and likewise could be one recess or a plurality of recesses, and could be positioned symmetrically or asymmetrically.

The sensor 200 includes a sensor die 210 and a plurality of wires 220 connected to the sensor die 210, as shown in FIG. 1. In an embodiment, the sensor die 210 is a pressure sensor, for example a piezoresistive pressure sensing die. In other embodiments, the sensor die 210 may be any other type of pressure sensor, or may be any sensor capable of detecting other qualities in addition to or alternatively to a pressure. The wires 220 are a plurality of conductors that transmit a signal of the sensor die 210 to an element external from the sensor assembly 10.

Assembly of the sensor assembly 10 will now be described in greater detail with reference to FIGS. 1, 6, and 7.

The sensor 200 is mounted in the sensor receiving space 160 on the base wall 110 and between the side walls 140 as shown in FIGS. 6 and 7. The sensor die 210 has a secured portion 212 disposed on the second base step section 126. In the shown embodiment, the secured portion 212 abuts against the base step 122 to locate the sensor die 210 in the sensor receiving space 160 along the longitudinal direction L.

As shown in FIGS. 6 and 7, a sensor adhesive 230 attaches the sensor die 210 to the carrier 100. The sensor adhesive 230 is deposited or dispensed over the secured portion 212 of the sensor die 210 and the wires 220. In the shown embodiment, the sensor adhesive 230 flows around the sensor die 210 and under the wires 220 to the position shown in FIG. 7, in which the sensor adhesive 230 is disposed between the inner base surface 112 of the rear base section 120 and the secured portion 212. In other embodiments, the sensor adhesive 230 may remain only on top of the sensor die 210 and the wires 220, or may be disposed both between the inner base surface 112 of the rear base section 120 and the secured portion 212 and on top of the sensor die 210 and the wires 220.

The sensor adhesive 230 may be any type of adhesive curable by a light, such as an epoxy curable by an ultraviolet light, may be any type of adhesive curable by the application of heat, or may be any type of adhesive curable by a chemical catalyst. The sensor adhesive 230, in a cured state, secures the secured portion 212 of the sensor die 210 and the wires 220 to the carrier 100. The sensor die 210 has a free portion 214 extending from the secured portion 212 and positioned over the sensing opening 118.

As shown in FIG. 6, the sensor die 210 is secured in a position spaced apart from the side walls 140 in the width direction W. The sensor die 210 is spaced by a first lateral gap distance G1 in the width direction W from the first side section 152 and by a second lateral gap distance G2 in the width direction W from the second side section 156. The second lateral gap distance G2 is greater than the first lateral gap distance G1. In the embodiment shown in FIGS. 6, the sensor adhesive 230 is disposed in an area between the side walls 140 and the sensor die 210 having the first lateral gap distance G1. In the embodiment shown in FIG. 6, the sensor die 210 is centered between the side walls 140 in the width direction W; the first lateral gap distance G1 is the same on both sides of the sensor die 210 and the second lateral gap distance G2 is the same on both sides of the sensor die 210. In other embodiments, the sensor die 210 may be positioned off-center between the side walls 140 in the width direction W, and the first lateral gap distance G1 and the second lateral gap distance G2 may be different on opposite sides of the sensor die 210 in the width direction W.

The positioning of the sensor die 210 with the first lateral gap distance G1 and the second lateral gap distance G2 from the side walls 140, and the omission of a front wall in the carrier 100, prevents the sensor die 210 from contacting the carrier 100. The second lateral gap distance G2 that is greater than the first lateral gap distance G1 is aligned with the free portion 214 of the sensor die 210 that is a sensing area of the sensor die 210. Limiting damage to the sensor die 210 and/or limiting output errors from the sensor die 210 by maintaining spacing from the carrier 100 in this manner helps to ensure accurate readings from the sensor die 210.

As shown in FIGS. 6 and 7, the wires 220 extend from the sensor die 210 over the first base step section 124 and out the proximal end 102 of the carrier 100. As in the shown embodiment, the wires 220 may also be secured to the inner base surface 112 of the base wall 110 by the sensor adhesive 230. In the shown embodiment, the sensor adhesive 230 is positioned in a portion of the first base step section 124. In another embodiment, the sensor adhesive 230 can be deposited within an entirety of the first base step section 124 and extends to the proximal end 102 of the carrier 100 or beyond the proximal end 102 of the carrier 100 in the longitudinal direction L.

In the embodiments shown in FIGS. 1-7, the carrier 100 is monolithically formed in a single piece. In another embodiment, the carrier 100 may be formed of a plurality of separate pieces, of the same material or of different materials, and assembled together to form the carrier 100 described above.

In an embodiment, the carrier 100 is formed from an at least partially translucent material, i.e. a translucent or a transparent material, such as polycarbonate. In an embodiment in which the carrier 100 is formed from an at least partially translucent material, the sensor adhesive 230 can be cured in the position shown in FIG. 7 by applying a light capable of curing the sensor adhesive 230, such as a light in the visible spectrum or an ultraviolet light, onto the carrier 100 such that the light passes through the at least partially translucent material of the carrier 100 and reaches the sensor adhesive 230.

In another embodiment, the carrier 100 may be formed from an opaque material. In this embodiment, the sensor adhesive 230 can be cured in the position shown in FIG. 7 by applying a heat to the sensor assembly 10 that cures the sensor adhesive 230, or can be cured in the position shown in FIG. 7 by a chemical catalyst, for example as a two-part epoxy.

Figure 8:
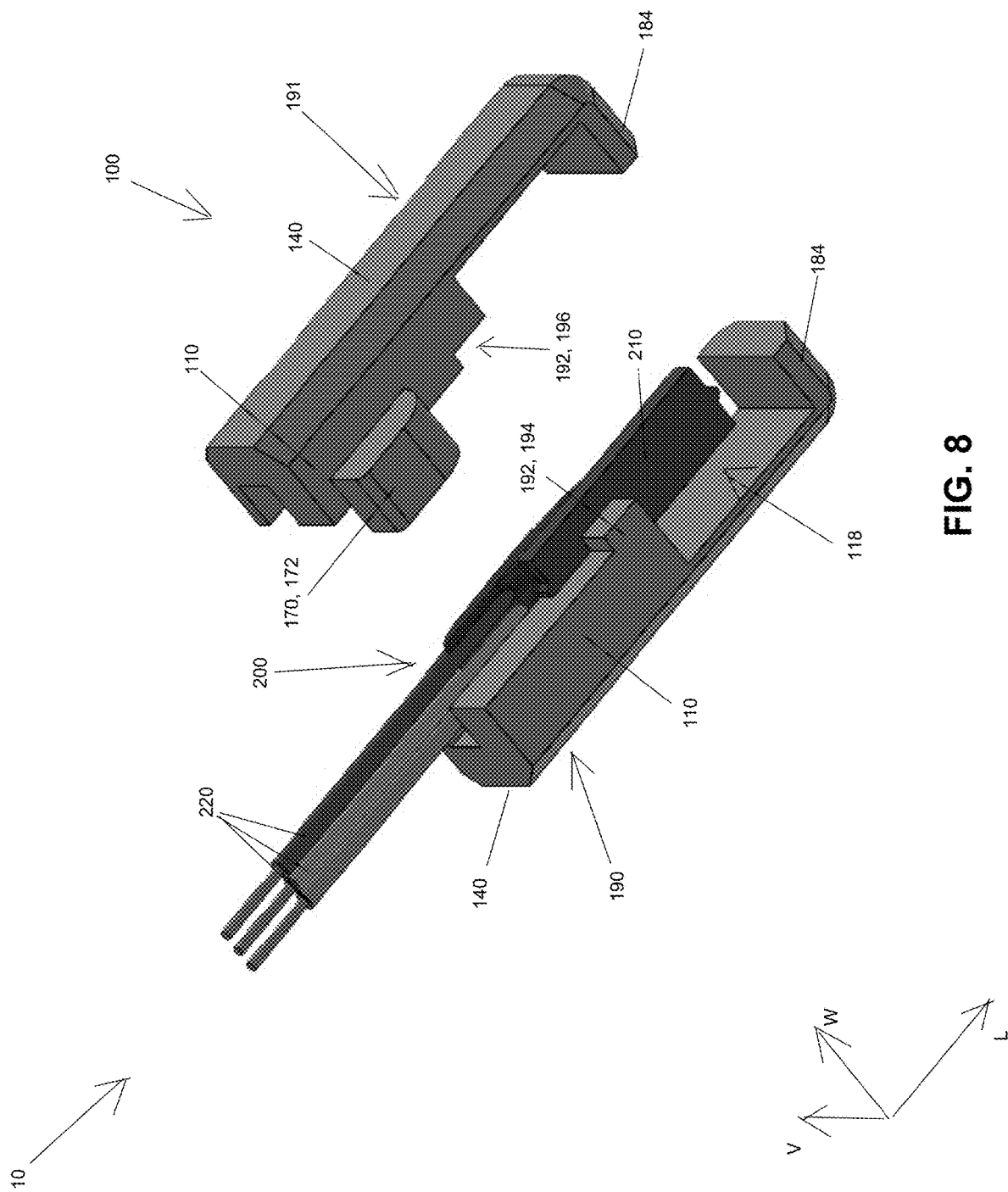
FIG. 8 is a perspective view of a sensor assembly according to another embodiment with a pair of shells separate from one another.
Figure 9:
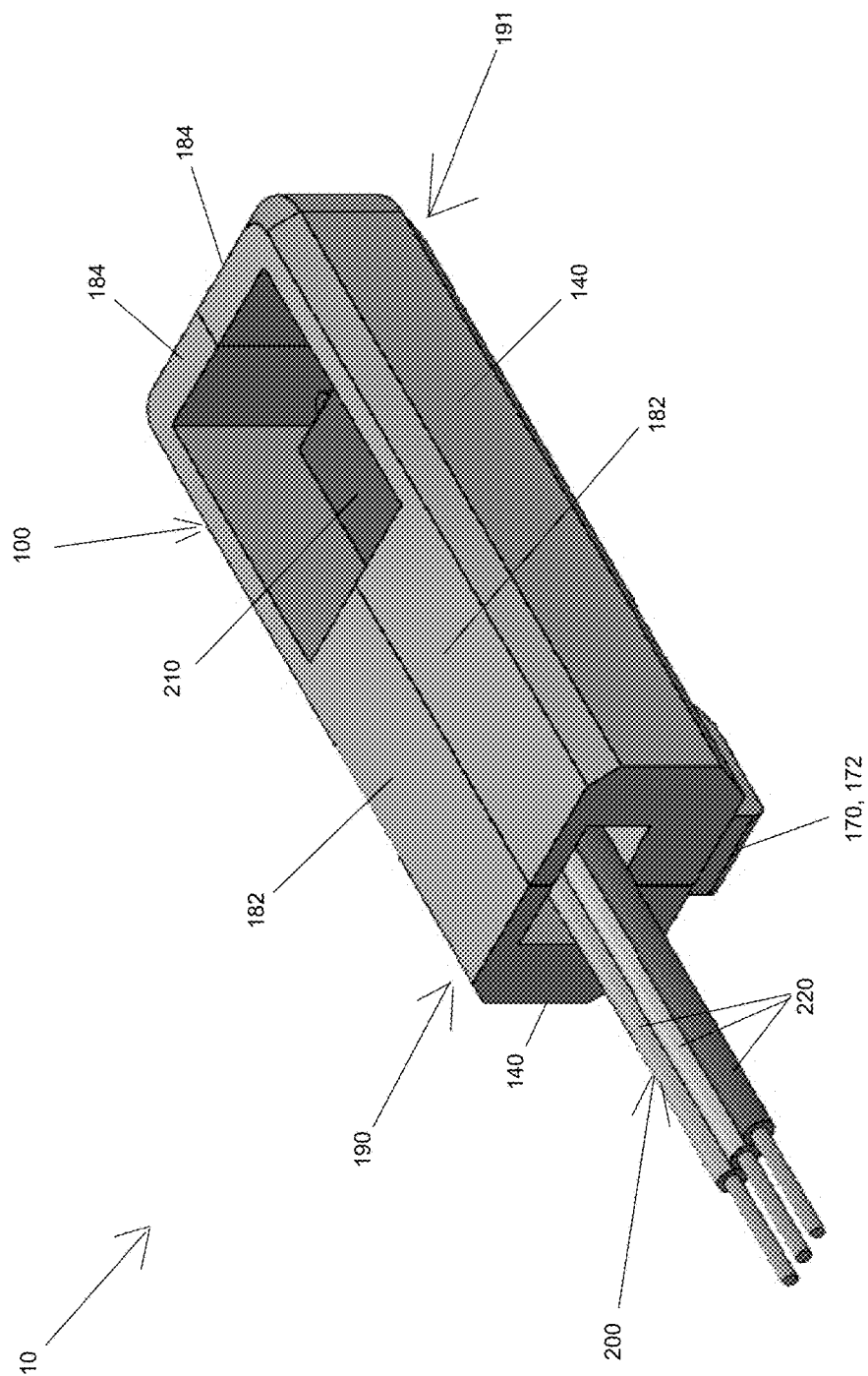
FIG. 9 is a perspective view of the sensor assembly of FIG. 8 with the pair of shells connected to one another.

In another embodiment, shown in FIGS. 8 and 9, the carrier 100 is formed of a pair of shells 190, 191 that are mateable together. The carrier 100 is shown formed from two shells 190, 191 in the embodiment of FIGS. 8 and 9. In other embodiments, the carrier 100 may be formed of more than two shells 190, 191. Each of the shells 190, 191 is monolithically formed in a single piece and may be formed of any material of the carrier 100 described above.

As shown in FIGS. 8 and 9, each of the shells 190, 191 has a portion of the base wall 110, including a portion of the sensing opening 118, and one of the side walls 140. In the embodiment shown in FIGS. 8 and 9, each of the shells 190, 191 also has a portion of a top wall 182 and a portion of an end wall 184 of the carrier 100. The carrier 100 may be formed of the pair of shells 190, 191 in other embodiments, such as the embodiments of FIGS. 1-7, in which the carrier 100 does not have the top wall 182 or the end wall 184. In other embodiments, the shells 190, 191 could be different segments of the carrier 100 separated along different directions, for example one of the shells 190 could have an entirety of the base wall 110 and the sensing opening 118 while the other of the shells 192 is a lid having at least the side walls 140.

In the embodiment shown in FIGS. 8 and 9, one of the shells 190, 191 has the carrier positioning device 170. In other embodiments, a portion of the carrier positioning device 170 could be positioned on each of the shells 190, 191. The carrier positioning device 170 is a peg 172 in the shown embodiment and, in other embodiments, could be any other type of protrusion or a recess extending through the base wall 110 as described above.

Each of the shells 190, 191, as shown in FIG. 8, has a locating feature 192. In the shown embodiment, a first shell 190 of the shells 190, 191 has a locating protrusion 194 extending from the portion of the base wall 110 and a second shell 191 of the shells 190, 191 has a locating recess 196 extending into the portion of the base wall 110. In the shown embodiment, the locating protrusion 194 is a single rectangular shaped protrusion and the locating recess 196 is a single rectangular shaped recess. In other embodiments, the locating protrusion 194 could be any other type of protrusion, such as a rounded protrusion, and the locating recess 196 could be any other type of recess, such as a concave divot, that corresponds to the locating protrusion 194. In another embodiment, one of the locating features 192 could have a plurality of locating protrusions 194 and the other of the locating features 192 could have a plurality of locating recesses 196.

To form the sensor assembly 10, the sensor 200 is first mounted on the base wall 110 of one of the shells 190, as shown in FIG. 8. The sensor 200 is mounted in position on the base wall 110 as described in detail with respect to FIGS. 6 and 7 above.

With the sensor 200 mounted to one of the shells 190, the carrier 100 is formed by moving the shells 190, 191 together along the width direction W to a formed state shown in FIG. 9. The locating features 192 cooperate with one another to ensure that the shells 190, 191 are in a proper position with respect to one another in the formed state; the locating protrusion 194 extends into the locating recess 196 in the shown embodiment. The portions of the shells 190, 191, such as the respective portions of the base wall 110, the top wall 182, and the end wall 184, abut one another as shown in FIG. 9 to form the walls 110, 182, 184 of the carrier 100 in the formed state. The shells 190, 191 can be attached to one another in the formed state shown in FIG. 9 by an adhesive, by plastic welding, or by any other form of attachment.

Figure 10:
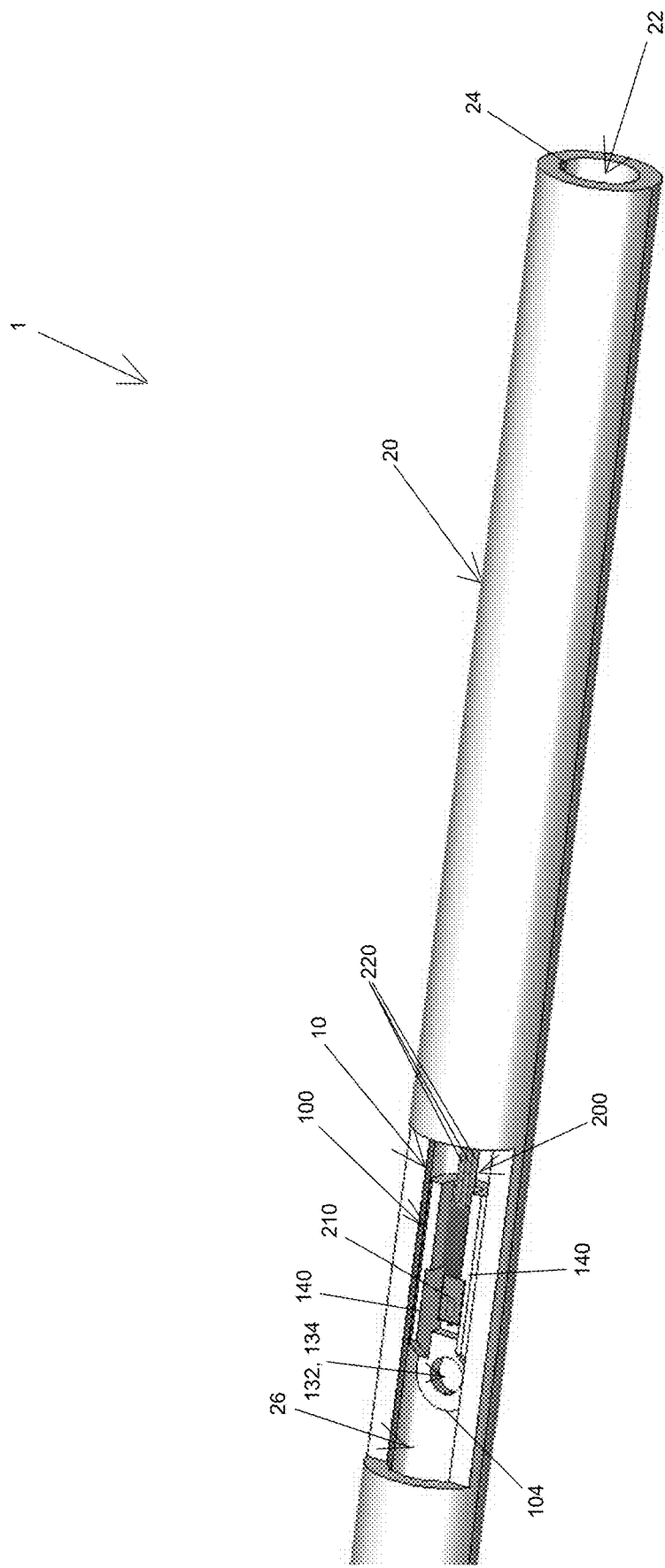
FIG. 10 is a perspective view of a sensing device according to an embodiment.
Figure 11:
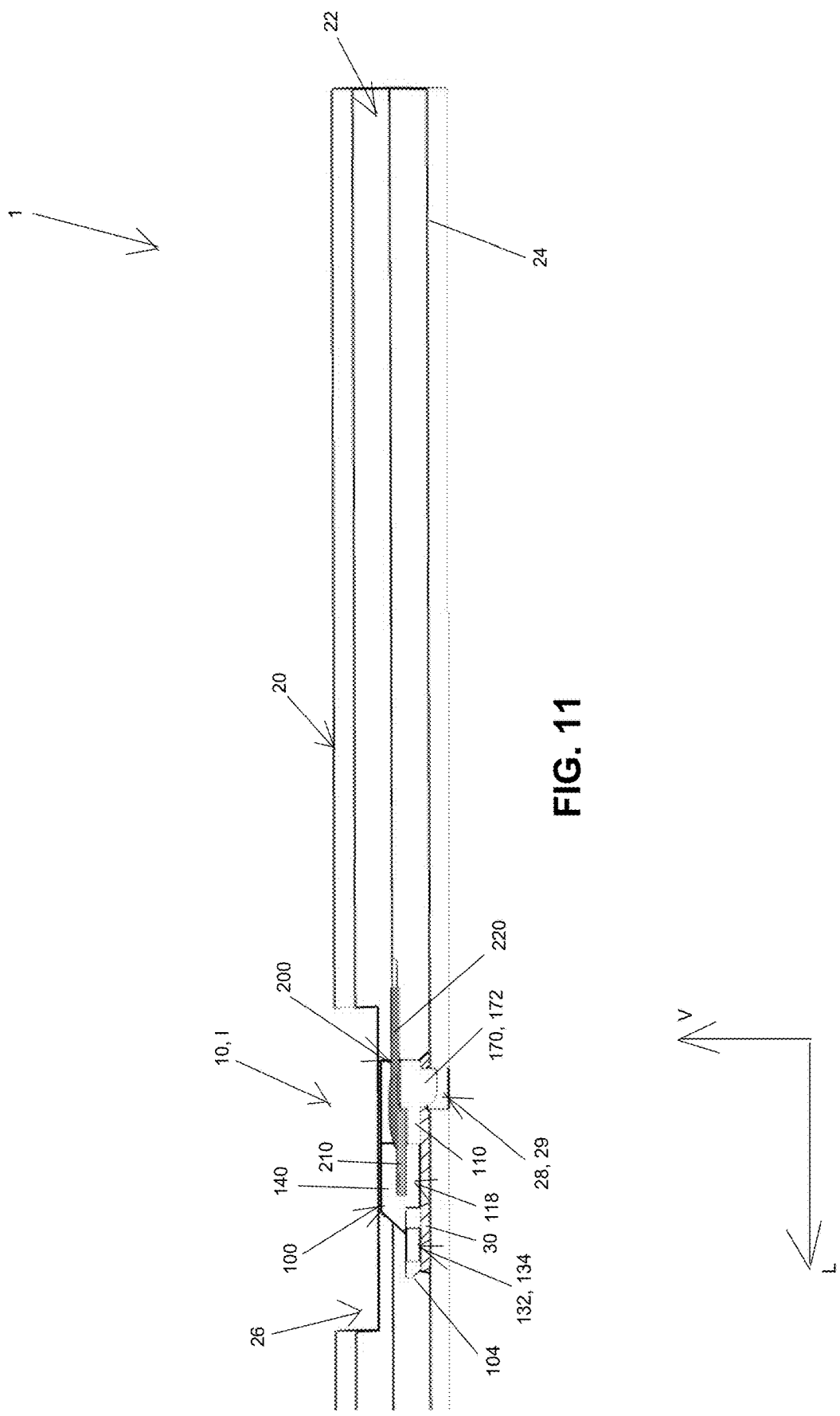
FIG. 11 is a sectional side view of the sensing device of FIG. 10.

A sensing device 1 according to an embodiment is shown in FIGS. 10 and 11. The sensing device 1 includes a body 20 and the sensor assembly 10 according to the embodiments described above disposed in the body 20. Not all of the elements of the sensor assembly 10 are labeled in detail in FIGS. 10 and 11 for clarity of the drawings, but the reference numbers and description of the sensor assembly 10 above with respect to FIGS. 1-3, 6, and 7 apply equally to the sensor assembly 10 shown in FIGS. 10 and 11.

The body 20, as shown in FIGS. 10 and 11, extends along the longitudinal direction L and has a receiving passageway 22 extending through the body 20 along the longitudinal direction L. An inner surface profile 24 of the body 20 forms and defines the receiving passageway 22. In the shown embodiment, the body 20 is a cylindrical member having a circular cross-section and the inner surface profile 24 has a circular cross-section. In other embodiments, the body 20 may be a tubular member having any cross-sectional shape, such as a square cross-section, a rectangular cross-section, or a curved cross-section other than a circle, and the inner surface profile 24 correspondingly may have any cross-sectional shape.

As shown in FIGS. 10 and 11, the body 20 has a sensing window 26 extending into the body 20 in the vertical direction V and communicating with the receiving passageway 22. The sensing window 26 extends along a portion of the body 20 along the longitudinal direction L.

As shown in FIG. 11, the body 20 has a body positioning device 28 opposite a portion of the sensing window 26 along the vertical direction V. In the shown embodiment, the body positioning device 28 is a recess 29 extending through the body 20. In the shown embodiment, the body positioning device 28 is a single recess 29 positioned approximately centrally on the body 20 along the longitudinal direction L; in other embodiments, the body positioning device 28 could be one recess 29 positioned off-center on the body 20 or could be a plurality of recesses 29 positioned symmetrically or asymmetrically on the body 20. In other embodiments, the body positioning device 28 may be a protrusion extending from the body 20 into the receiving passageway 22 along the vertical direction V, and likewise could be one protrusion or a plurality of protrusions, and could be positioned symmetrically or asymmetrically.

The installation of the sensor assembly 10 in the body 20 to form the sensing device 1 will now be described in greater detail with respect to FIGS. 10 and 11.

The sensor assembly 10, formed as any of the embodiments described above with respect to FIGS. 1-9, is positioned at an end of the receiving passageway 22 of the body 20. A tool is attached to the pulling device 132 at the distal end 104 of the carrier 100. The tool may be a wire or a protrusion passing through or otherwise engaging the eyelet 134 formed as the pulling device 132 in the embodiment shown in FIGS. 10 and 11. In another embodiment in which the pulling device 132 is the hook 136, as shown in FIGS. 4 and 5 and described above, the tool may be a wire or a catch engaging the hook 136.

The sensor assembly 10 is pulled into and along the receiving passageway 22 in the longitudinal direction L by the pulling device 132 and using the tool. The profiled side edges 146 of the side walls 140 and the profiled base edges 116 of the base wall 110 are shaped to correspond to the inner surface profile 24 of the body 20, such that the carrier 100 can fit in the receiving passageway 22 and move along the receiving passageway 22 without significant obstruction.

Pulling the sensor assembly 10 into the body 20 by the pulling device 132 limits damage to the sensor die 210 by applying the pulling force on the carrier 100. Further, as the carrier 100 fits in the receiving passageway 22, the carrier 100 protects the sensor die 210 from contact with the body 20 as the sensor assembly 10 is moved. The use of the pulling device 132 to move the sensor assembly 10 also allows the wires 220 to remain connected to the sensor die 210 and sensor conditioning electronics, and prevents additional steps from complicating the assembly process.

The sensor assembly 10 is pulled along the receiving passageway 22 until the carrier positioning device 170 reaches the body positioning device 28, as shown in FIG. 11. The carrier positioning device 170 cooperates with the body positioning device 28 to position the sensor assembly 10 in an installed position I in the receiving passageway 22. In the shown embodiment, the carrier positioning device 170 embodied as the peg 172 engages the body positioning device 28 embodied as the recess 29. In another embodiment, the body positioning device 28 may be the peg extending into the receiving passageway 22 and the carrier positioning device 170 may be the recess receiving the peg. In embodiments in which the carrier positioning device 170 and the body positioning device 28 are each a plurality of elements, the carrier positioning device 170 and the body positioning device 28 have the same number of elements and the elements individually correspond in position to engage one another.

Figure 12:
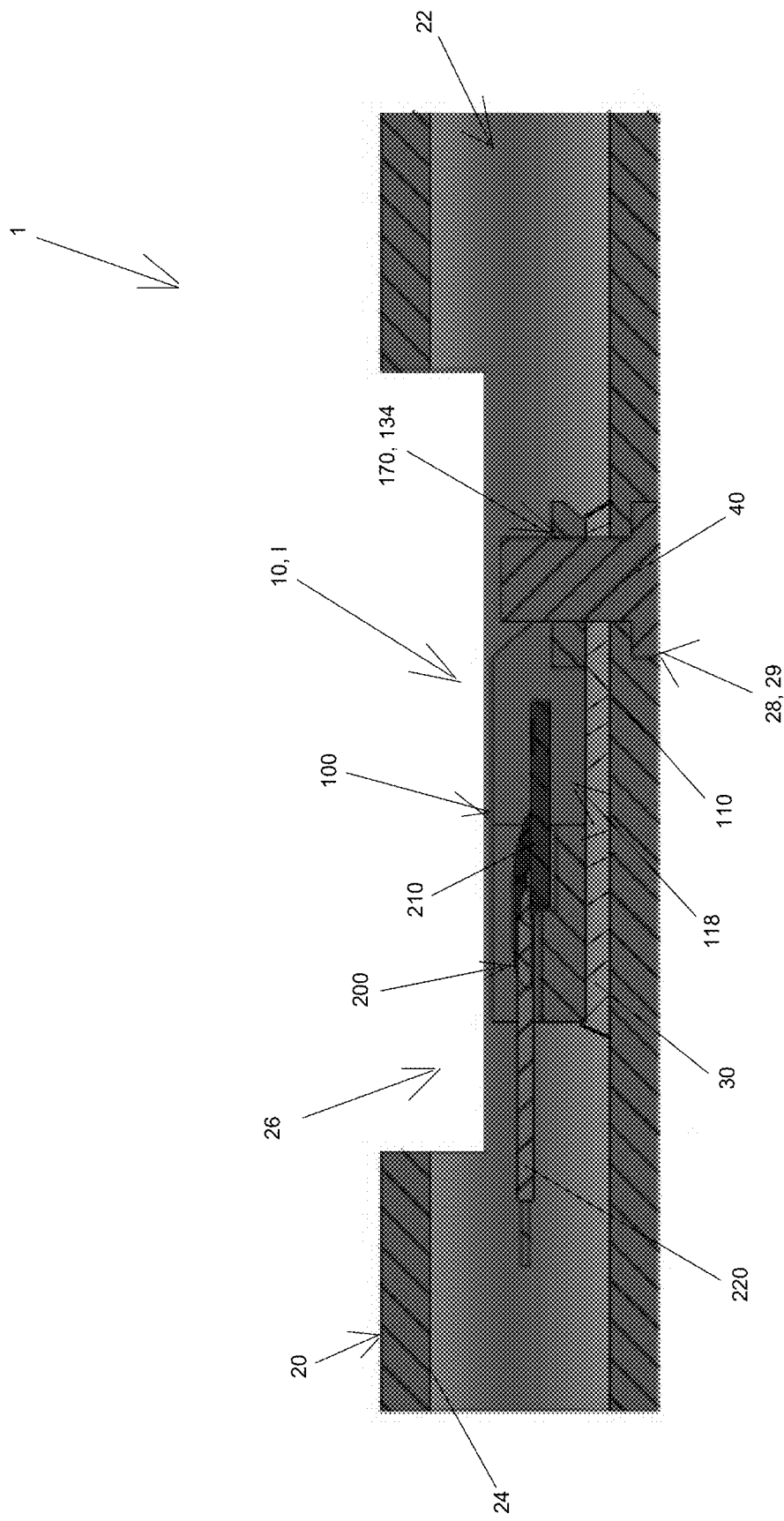
FIG. 12 is a sectional side view of a sensing device according to another embodiment.

In another embodiment, shown in FIG. 12, the carrier positioning device 170 is the eyelet 134 extending through the base wall 110. In this embodiment, when the eyelet 134 is aligned with the recess 29 of the body positioning device 28 along the vertical direction V, a pin 40 is inserted to extend through the recess 29 and the eyelet 134 to secure the sensor assembly 10 in the installed position I. In other embodiments, an eyelet or passageway positioned elsewhere on the base wall 110 may receive the pin 40.

Once the sensor assembly 10 is in the installed position I in the receiving passageway 22, a device adhesive 30 is applied as shown in FIGS. 11 and 12 to secure the sensor assembly 10 in the installed position I. The device adhesive 30 is disposed between the carrier 100 and the body 20 around the carrier positioning device 170 and the body positioning device 28. The device adhesive 30 may be an epoxy or any other type of adhesive, and may be curable by light, including light in the visible spectrum or ultraviolet light, heat, or by chemical catalysts. The engagement of the carrier positioning device 170 with the body positioning device 28 ensures that the carrier 100 and the sensor 200 held by the carrier 100 are properly positioned within the body 20 prior to applying the device adhesive 30.

In an embodiment, the sensing device 1 is part of a catheter used in medical applications. In this embodiment, the sensor die 210 can be used to detect a pressure of a fluid, the fluid contacting the sensor die 210 by passing through the sensing window 26 and into the receiving passageway 22, and can transmit a signal representing the pressure along the wires 220. In other embodiments, the sensing device 1 could be another type of medical device, or could be part of any device requiring the sensor 200 to be disposed in the body 20 to measure pressure or other qualities.

What is claimed is:

1. A sensor assembly, comprising:
   a carrier having a base wall and a pair of side walls extending from the base wall, each of the side walls has a side step between a first side section and a second side section extending from the first side section along a longitudinal direction of the carrier; and
   a sensor mounted on the base wall between the side walls, a sensor die of the sensor is spaced in a width direction perpendicular to the longitudinal direction by a first lateral gap distance from the first side section and by a second lateral gap distance from the second side section, the second lateral gap distance is greater than the first lateral gap distance.

2. The sensor assembly of claim 1, wherein the base wall extends from a proximal end to a distal end along the longitudinal direction, the base wall has a rear base section at the proximal end and a front base section at the distal end separated from one another along the longitudinal direction by a sensing opening in the base wall.

3. The sensor assembly of claim 2, wherein the sensor die has a secured portion attached to the rear base section by a sensor adhesive.

4. The sensor assembly of claim 3, wherein the sensor die has a free portion extending from the secured portion and positioned over the sensing opening.

5. The sensor assembly of claim 3, wherein the rear base section has a base step between a first base step section at the proximal end and a second base step section extending from the first base step section, the first base step section has a first base thickness and the second base step section has a second base thickness, the first base thickness is greater than the second base thickness.

6. The sensor assembly of claim 5, wherein the secured portion is disposed on the second base step section.

7. The sensor assembly of claim 2, wherein the carrier has a pulling device in the front base section.

8. The sensor assembly of claim 2, wherein the carrier has a carrier positioning device in the rear base section.

9. The sensor assembly of claim 1, wherein the carrier is formed from an at least partially translucent material.

10. The sensor assembly of claim 1, wherein each of the side walls has a profiled side edge at a free end of the side walls opposite the base wall.

11. The sensor assembly of claim 1, wherein the carrier is monolithically formed in a single piece.

12. The sensor assembly of claim 1, wherein the carrier is formed of at least a pair of shells that are mateable together, each of the shells has one of the side walls and a portion of the base wall.

13. A sensing device, comprising:
a body having a receiving passageway extending through the body; and
a sensor assembly including a carrier and a sensor mounted on the carrier, the carrier has a base wall extending from a proximal end to a distal end along a longitudinal direction and a pair of side walls extending from the base wall, the sensor is mounted on the base wall between the side walls, the carrier has a pulling device at the distal end of the base wall by which the sensor assembly is pulled into and along the receiving passageway in the longitudinal direction.

14. The sensing device of claim 13, wherein the pulling device is an eyelet extending through the base wall.

15. The sensing device of claim 13, wherein the pulling device is a hook extending from an inner base surface of the base wall.

16. The sensing device of claim 13, wherein the carrier has a carrier positioning device on the base wall and the body has a body positioning device cooperating with the carrier positioning device to position the sensor assembly in the receiving passageway.

17. The sensing device of claim 16, further comprising a device adhesive disposed between the carrier and the body around the carrier positioning device and the body positioning device.

18. The sensing device of claim 16, wherein the carrier positioning device is a peg extending from an outer base surface of the base wall and the body positioning device is a recess extending through the body, the peg engages the recess.

19. The sensing device of claim 16, wherein the carrier positioning device is an eyelet extending through the base wall and the body positioning device is a recess extending through the body, and further comprising a pin extending through the eyelet and the recess.

20. The sensing device of claim 13, wherein each of the side walls has a profiled side edge at a free end of the side walls opposite the base wall, the profiled side edge corresponds to an inner surface profile of the body forming the receiving passageway.

* * * * *